United States Patent [19]

Wu

[11] Patent Number: 5,221,775
[45] Date of Patent: Jun. 22, 1993

[54] ETHYLENE DIMERIZATION
[75] Inventor: An-Hsiang Wu, Bartlesville, Okla.
[73] Assignee: Phillips Petroleum Company, Bartlesville, Okla.
[21] Appl. No.: 854,137
[22] Filed: Mar. 19, 1992
[51] Int. Cl.$^5$ .................................................. C07C 2/08
[52] U.S. Cl. ...................................... 585/520; 585/523; 585/527; 585/530; 585/531; 502/325
[58] Field of Search ............... 585/514, 511, 521, 510, 585/523, 531, 520, 530

[56] References Cited
U.S. PATENT DOCUMENTS 4,487,847 12/1984 Knudsen ............................ 502/155
4,528,415 7/1985 Knudsen ............................ 585/527
4,709,112 11/1987 Sato et al. ......................... 585/573

Primary Examiner—Asok Pal
Assistant Examiner—P. Achutamurthy
Attorney, Agent, or Firm—William R. Sharp

[57] ABSTRACT

An ethylene dimerization process is provided wherein ethylene is contacted with an organonickel (0) compound and a phosphine compound in a fluorinated alcohol solvent to produce a precursor reaction mixture, followed by contacting ethylene with the precursor reaction mixture and a fluorinated organoacid to produce a product reaction mixture comprising a $C_4$ fraction of predominantly 2-butenes.

17 Claims, No Drawings

ETHYLENE DIMERIZATION

This invention relates to a process for dimerizing ethylene to butenes, comprising predominantly 2-butenes.

2-butenes are useful in metathesis processes to produce other olefins such as propylene, and are also useful in alkylation processes in the production of motor fuels. It would be desirable to provide a process of dimerizing ethylene to butenes which achieves a combination of high productivity and high selectivity to 2-butenes.

It is, therefore, an object of this invention to provide an improved process for dimerizing ethylene which achieves the above-mentioned desired combination of results.

The above object is realized by a process comprising: (a) contacting ethylene, an organonickel(0) compound (having nickel at a valence state of 0) and a phosphine compound of the formula $PR_3$ where R independently represents H or a $C_1$ to $C_{20}$ hydrocarbyl radical and where at least one R is not H, wherein the ethylene is in a gaseous phase and the organonickel(0) compound and phosphine compound are in a liquid phase and in a fluorinated alcohol solvent of the formula $R_3'COH$ where R' independently represents H, F or a $C_1$ to $C_{12}$ fluorinated or nonfluorinated alkyl, cycloalkyl, aryl, alkaryl, or aralkyl radical and where at least one R' is F or said fluorinated radical, thereby producing a precursor reaction mixture in a liquid phase; and (b) contacting, after step (a), ethylene in a gaseous phase, the precursor reaction mixture, and a fluorinated organoacid in a liquid phase, thereby producing a product reaction mixture in a liquid phase comprising said butenes. The fluorinated organoacid in step (b) can, if desired, also be in a fluorinated alcohol solvent of the above-mentioned formula, in which case such solvent can be the same as or different than the fluorinated alcohol solvent employed in step (a).

Suitable fluorinated alcohol solvents include 2,2,2-trifluoroethanol, 2,2,3,3,3-pentafluoro-1-propanol and 2,2,3,3,4,4,4-heptafluoro-1-butanol. The presently preferred fluorinated alcohol is 2,2,2-trifluoroethanol. The weight ratio of the total amount of fluorinated alcohol solvent employed in the process to the combination of the organonickel(0) compound, phosphine compound and fluorinated organoacid can be in the broad range of about $1-10^6$ to 1, most preferably in the range of about 5-10,000 to 1. Practical considerations such as cost and reactor size are factors in determining the amount of solvent employed.

Suitable organonickel(0) compounds include bis(1,5-cyclooctadiene)nickel(0), tetrakis(triphenylphosphine)nickel(0), bis(triphenylphosphine)nickel(0) dicarbonyl and nickel(0) tetracarbonyl. Bis(1,5-cyclooctadiene)nickel(0) is particularly preferred. The organonickel(0) compounds are typically in anhydrous form.

Suitable phosphine compounds include cyclohexylphosphine, dicyclohexylphosphine, tricyclohexylphosphine, triethylphosphine, triisopropylphosphine, triisobutylphosphine, tri-n-butylphosphine, tri-t-butylphosphine, phenylphosphine, diphenylphosphine, triphenylphosphine, diphenylcyclohexylphosphine, diethylphenylphosphine, ortho-tolyldiphenylphosphine, di(ortho-tolyl)phenylphosphine and tribenzylphosphine.

The preferred fluorinated organoacid is a fluorinated carboxylic acid of the formula R"COOH where R" represents a $C_1$ to $C_{10}$ fluorinated hydrocarbyl radical having at least one fluorine (F) atom. Suitable fluorinated carboxylic acids include trifluoroacetic acid, heptafluorobutyric acid, difluoroacetic acid, pentafluoropropionic acid and perfluoroadipic acid. The preferred fluorinated carboxylic acid is trifluoroacetic acid. Fluorinated organoacids also within the scope of certain broad aspects of the invention are fluorinated sulfonic acids such as trifluoromethanesulfonic acid and heptafluoroethanesulfonic acid.

With respect to molar ratios of the various reagents, the molar ratio of the phosphine compound to the organonickel(0) compound is preferably about 0.1-5 to 1, most preferably about 0.8-1.2 to 1, and the molar ratio of the fluorinated organoacid to the organonickel(0) compound is preferably about 0.5-20 to 1, most preferably about 1-5 to 1.

The particular procedure by which the various reagents are contacted as in (a) and (b) above can take a variety of forms.

In accordance with step (a), the organonickel(0) compound and phosphine compound in the fluorinated alcohol solvent and in liquid phase can be contacted with ethylene in gaseous phase in a first vessel by agitating the liquid phase therein and pressuring the first vessel with the ethylene to a predetermined pressure.

In accordance with step (b), the acid (optionally in a fluorinated alcohol solvent) can be added to a second vessel, and either the precursor reaction mixture resulting from step (a) can be transferred from the first vessel to the second vessel or the acid can be transferred to the first vessel. In either case, the precursor reaction mixture and acid are preferably agitated in whichever vessel receives all liquid reagents and such vessel is pressured with ethylene to a predetermined reaction pressure. Most preferably, the acid is contacted with ethylene in the second vessel prior to contacting with the precursor reaction mixture.

The vessel in which step (b) is carried out can be an autoclave or other similar pressure reactor, and the vessel in which step (a) is carried out can be such a reactor or an associated addition vessel, depending on the particular procedure employed.

Pressure and temperature conditions in steps (a) and (b) are such that the ethylene is in a gaseous phase and the organonickel(0) compound and phosphine compound as in the fluorinated alcohol solvent and the acid, optionally in a fluorinated alcohol solvent, are in the liquid phase. Preferably, step (a) is carried out at a pressure of about 5 to 5000 psig and a temperature of about $-100°$ C. to about $50°$ C., most preferably at a pressure of about 20 to about 1000 psig and a temperature of about $15°$ C. to about $35°$ C. (generally ambient temperature conditions). Step (b) is preferably carried out at a pressure of about 5 to about 5000 psig and a temperature of about $0°$ C. to about $125°$ C., most preferably at a pressure of about 200 to about 1000 psig and a temperature of about $20°$ C. to about $50°$ C.

With respect to time, step (a) is preferably carried out for a time of about 1 minute to about 2 hours, most preferably about 3 minutes to about 1 hour. Step (b) is preferably carried out for a time of about 1 minute to about 3 hours, most preferably about 5 minutes to about 1 hour.

The butenes as contained in the product reaction mixture resulting from step (b) can be separated and recovered from the product reaction mixture by conventional means such as fractional distillation. As demonstrated in examples to follow, such butenes are predominantly (at least about 90 weight percent) 2-butenes. In addition to a high selectivity to 2-butenes, very high productivities are obtained in accordance with the invention.

Many variations of the invention are possible in light of the above teachings. For example, although the invention is described above in terms of a batchwise process, it is within the scope of certain broad aspects of the invention to employ a continuous process wherein ethylene is passed continuously into a reaction zone while product reaction mixture containing the butenes is concomitantly withdrawn therefrom.

An example will now be described to further illustrate the invention, but which should not be construed to limit the invention in any manner.

EXAMPLE

The purpose of this example is to demonstrate the dimerization of ethylene in accordance with the invention employing bis(1,5-cyclooctadiene)nickel(0), a variety of phosphine compounds and trifluoroacetic acid in a fluorinated alcohol solvent.

This example employed a 300 mL stainless steel (316SS) Autoclave Engineers stirred tank autoclave, hereafter denoted simply as a reactor, and a 40 mL addition vessel connected to the reactor by means of an addition valve. It is understood that the contents of the reactor are being agitated, typically at a slow agitation of about 300 rpm during purging of the reactor or addition of various reagents to the reactor and at a normal agitation of about 1600 rpm at all other times.

Runs 1-7, employing different phosphine compounds, were carried out following the procedure described below.

The reactor was purged with nitrogen for 5 minutes followed by addition of 48 mL of 2,2,2-trifluoroethanol, a phosphine compound (1.0 mmol) shown in the Table and bis(1,5-cyclooctadiene)nickel(0) (0.275 g; 1.0 mmol) which was weighed in an argon-filled box. The reactor was then sealed, purged with ethylene at least four times, and then pressured with ethylene to 50 psig for 5 minutes. All of the above steps were undertaken at ambient temperature (about 25° C.).

A solution of trifluoroacetic acid (0.114 g; 1.0 mmol) in 2 mL of 2,2,2-trifluoroethanol was added to the addition vessel using a syringe. The addition vessel was immediately sealed and pressured to 700 psig with ethylene. The contents of the addition vessel, including the ethylene, were then transferred to the reactor at the end of the above-mentioned 5 minute period through the addition valve. Reaction proceeded immediately, evidenced by the rise in reaction temperature. The reaction temperature was controlled at a temperature of about 40° C. by the use of external cooling water. The internal reactor pressure was maintained at 700 psig and the reaction was continued for a time of about 10 minutes.

At the end of such reaction time, an approximately 5 gram sample of the resulting product reaction mixture was taken from the reactor through its sample valve into a 50 mL pressure sample tube. The sample was analyzed with an HP 5890 II GC-FID Spectrometer equipped with a capillary DB-1 (60 m) column. The column was operated at 30° C. for 5 minutes, followed by a 15° C./minute increase to 285° C. which was held for 13 minutes. Detection was obtained using a flame ionization detector in the area percent mode. Selectivity and weight percent $C_4$, discussed further below, were determined from spectra as recorded by the spectrometer.

Results are reported in the Table in terms of productivity, weight percent $C_4$ and selectivity to 2-butenes, with the respective weight percentages of trans-2 and cis-2-butenes of total 2-butenes shown in parentheses. Productivity is defined as the grams of oligomerization product (olefinic oligomers of ethylene, i.e. $C_nH_{2n}$, or simply "$C_n$", where n=4,6...) produced per gram of Ni per hour, and was calculated in each example based on grams of ethylene reacted. Weight percent $C_4$ is the weight percent of the dimer $C_4$ of the total oligomerization product. Selectivity to 2-butenes is given in terms of the weight percent of the total $C_4$ fraction.

TABLE

| Run | Phosphine | Productivity | Wt. % $C_4$ | Selectivity wt. % 2-butenes (trans-2/cis-2) |
|---|---|---|---|---|
| 1 | Tricyclohexylphosphine | 20,580 | 95 | 90(60/40) |
| 2 | Dicyclohexylphosphine | 27,500 | 90 | 97(60/40) |
| 3 | Cyclohexylphosphine | 20,350 | 92 | 90(64/36) |
| 4 | Phenylphosphine | 15,600 | 91 | 94(71/29) |
| 5 | Diphenylphosphine | 27,500 | 90 | 97(60/40) |
| 6 | Triphenylphosphine | 20,350 | 92 | 90(64/36) |
| 7 | Tri-n-butylphosphine | 15,600 | 91 | 94(71/29) |

The results in the Table show very high productivities of over 15,000 g/g/hr, a weight percent of $C_4$ of the total oligomerization product of at least 90 weight percent, and selectivity to 2-butenes of at least 90 weight percent of the $C_4$ fraction.

That which if claimed is:

1. A process for dimerizing ethylene to butenes comprising:
    (a) contacting ethylene, an organonickel(0) compound and a phosphine compound of the formula $PR_3$ where R independently represents H or a $C_1$ to $C_{20}$ hydrocarbyl radical and where at least one R is not H, wherein the ethylene is in a gaseous phase and the organonickel(0) compound and phosphine compound are in a liquid phase and in a fluorinated alcohol solvent of the formula $R_3'COH$ where R' independently represents H, F or a $C_1$ to $C_{12}$ fluorinated or nonfluorinated alkyl, cycloalkyl, aryl, alkaryl, or aralkyl radical and where at least one R' is F or said fluorinated radical, thereby producing a precursor reaction mixture in a liquid phase;
    (b) contacting, after step (a), ethylene in a gaseous phase, the precursor reaction mixture, and a fluorinated organoacid in a liquid phase, thereby producing a product reaction mixture in a liquid phase comprising said butenes.

2. A process as recited in claim 1 wherein in step (b) the fluorinated organoacid is also in a fluorinated alcohol solvent of the formula $R_3'COH$.

3. A process as recited in claim 2 wherein the fluorinated alcohol solvent in which the organonickel(0) compound and phosphine compound are present in step (a) is 2,2,2-trifluoroethanol.

4. A process as recited in claim 3 wherein the fluorinated alcohol solvent in which the fluorinated organoacid is present in step (b) is also 2,2,2-trifluoroethanol.

5. A process as recited in claim 2 wherein the weight ratio of the total fluorinated alcohol solvent in said process to the combination of the organonickel(0) compound, phosphine compound and fluorinated organoacid is in the range of about 5-10,000 to 1.

6. A process as recited in claim 1 wherein the organonickel(0) compound is selected from the group consisting of bis(1,5-cyclooctadiene)nickel(0), tetrakis(triphenylphosphine)nickel(0), bis(triphenylphosphine)nickel(0) dicarbonyl and nickel(0) tetracarbonyl.

7. A process as recited in claim 6 wherein the organonickel(0) compound is bis(1,5-cyclooctadiene)nickel(0).

8. A process as recited in claim 1 wherein the fluorinated organoacid is a fluorinated carboxylic acid of the formula R"COOH where R" represents a $C_1$ to $C_{10}$ fluorinated hydrocarbyl radical having at least one fluorine (F) atom.

9. A process as recited in claim 8 wherein the fluorinated organoacid is trifluoroacetic acid.

10. A process as recited in claim 1 wherein the molar ratio of the phosphine compound to the organonickel(0) compound is about 0.1–5 to 1, and the molar ratio of the fluorinated organoacid to the organonickel(0) compound is about 0.5–20 to 1.

11. A process as recited in claim 1 wherein step (a) is carried out at a pressure of about 5 to about 5000 psig, at a temperature of about $-100°$ C. to about 50° C., and for a time of about 1 minute to about 2 hours.

12. A process as recited in claim 11 wherein step (a) is carried out at a pressure of about 20 to about 1000 psig, at a temperature of about 15° C. to about 35° C., and for a time of about 3 minutes to about 1 hour.

13. A process as recited in claim 1 wherein step (b) is carried out at a pressure of about 5 to about 5000 psig, at a temperature of about 0° C. to about 125° C., and for a time of about 1 minute to about 3 hours.

14. A process as recited in claim 13 wherein step (b) is carried out at a pressure of about 200 to about 1000 psig, at a temperature of about 20° C. to about 50° C., and for a time of about 5 minutes to about 1 hour.

15. A process as recited in claim 1 wherein the fluorinated organoacid is contacted with ethylene prior to step (b).

16. A process for dimerizing ethylene to butenes consisting essentially of:
(a) contacting ethylene, an organonickel(0) compound, and a phosphine compound of the formula $PR_3$ where R independently represents H or a $C_1$ to $C_{20}$ hydrocarbyl radical and where at least one R is not H, wherein the ethylene is in a gaseous phase and the organonickel(0) compound and phosphine compound are in a liquid phase and in a fluorinated alcohol solvent of the formula $R_3'COH$ where R' independently represents H, F, or a $C_1$ to $C_{12}$ fluorinated or nonfluorinated alkyl, cycloalkyl, aryl, alkaryl, or aralkyl radical and where at least one R' is F or said fluorinated radical, thereby producing a precursor reaction mixture in a liquid phase; and
(b) contacting, after step (a), ethylene in a gaseous phase, the precursor reaction mixture, and a fluorinated organoacid in a liquid phase and in a fluorinated alcohol solvent of said formula $R_3'COH$, thereby producing a product reaction mixture in a liquid phase comprising said butenes.

17. A process for dimerizing ethylene to butenes comprising:
(a) contacting ethylene, bis(1,5-cyclooctadiene)nickel(0), and a phosphine compound of the formula $PR_3$ where R independently represents H or a $C_1$ to $C_{20}$ hydrocarbyl radical and where at least one R is not H, wherein the ethylene is in a gaseous phase and the bis(1,5-cyclooctadiene)nickel(0) and phosphine compound are in a liquid phase and in 2,2,2-trifluoroethanol solvent, thereby producing a precursor reaction mixture in a liquid phase;
(b) contacting, after step (a), ethylene in a gaseous phase, the precursor reaction mixture, and trifluoroacetic acid in a liquid phase, thereby producing a product reaction mixture in a liquid phase comprising said butenes.

* * * * *